United States Patent

Ahonen et al.

[11] Patent Number: 6,137,894
[45] Date of Patent: *Oct. 24, 2000

[54] ON-LINE METHOD FOR DETERMINING THE WOOD-BARK RATIO FROM A FLOW OF MATERIAL

[75] Inventors: Mikko Ahonen, Vaajakoski; Kalevi Pietikäinen, Jyväskylä ; Jari Suuronen, Vihijäryi; Pekka Silvennoinen; Veli Juhani Aho, both of Jyväskylä, all of Finland

[73] Assignee: Valtion teknillinen tutkimuskeskus, Espoo, Finland

[ * ] Notice: This patent issued on a continued prosecution application filed under 37 CFR 1.53(d), and is subject to the twenty year patent term provisions of 35 U.S.C. 154(a)(2).

[21] Appl. No.: 08/937,324

[22] Filed: Sep. 18, 1997

[30] Foreign Application Priority Data

Sep. 19, 1996 [FI] Finland ..................................... 963714

[51] Int. Cl.[7] ....................................................... G06K 9/00
[52] U.S. Cl. .......................................... 382/110; 356/237.1
[58] Field of Search ..................................... 382/110, 228; 250/559.04, 559.05, 559.06, 559.24, 559.25, 223 R, 208.1; 356/446, 432, 237.1, 369, 431, 445; 348/91, 128, 82, 132

[56] References Cited

U.S. PATENT DOCUMENTS

| | | | |
|---|---|---|---|
| 4,221,974 | 9/1980 | Mueller et al. | 250/563 |
| 4,266,675 | 5/1981 | Barwise | 250/223 R |
| 4,992,949 | 2/1991 | Arden | 209/518 |
| 5,274,244 | 12/1993 | Johansson et al. | 250/559.25 |
| 5,335,790 | 8/1994 | Geiger et al. | 209/518 |
| 5,394,342 | 2/1995 | Poon | 382/110 |

*Primary Examiner*—Amelia Au
*Assistant Examiner*—Samir Ahmed
*Attorney, Agent, or Firm*—Fildes & Outland, P.C.

[57] ABSTRACT

An on-line method for determining the wood-bark ratio in a flow of material containing both wood and bark includes illuminating the flow of material and scanning using a CCD camera, by means of which 30–300 image pixels/cm are obtained in the transverse direction of the flow of material. Narrow transverse groups of 1–20 adjacent pixels, in which the brightness of the pixels deviates from a preset criterium are filtered out of the transverse group of pixels and the calculation of the wood-bark ratio of the photographs takes place without these narrow groups.

10 Claims, 1 Drawing Sheet

ON-LINE METHOD FOR DETERMINING THE WOOD-BARK RATIO FROM A FLOW OF MATERIAL

FIELD OF THE INVENTION

This invention relates to an on-line method and equipment for determining the wood-bark ratio from a flow of material containing timber and bark.

BACKGROUND OF THE INVENTION

At present, whole-wood chips or surface plank chips are cleaned, to make them suitable for use in the manufacture of pulp. Reliable measurement of the bark content is essential to the operation of chip-cleaning equipment, so that the equipment can be adjusted. Correspondingly, it is essential to the optimal operation of a debarking plant to be able to measure reliably the wood content of bark material, so that the plant can be operated as efficiently as possible, without unreasonably increasing wood waste. Finnish Patent 90918 describes a method for determining the bark/wood ratio from a sample. Naturally, this method cannot be applied to on-line operation. The basis of the patent application was the observation, made at the time, that the image of woodchip or bark material did not, as such, give a reliable result of the ratio in question, on the basis of the degree of light. This was because the dispersion of the samples was too great. Thus, according to the invention, the material was ground to a small granule size, when reliable and repeatable measurements could be made from this ground material.

Swedish publication print 466420 (FI app. 922179) describes a continuously operating method, by means of which it is possible to show the presence of bark, or determine the degree of debarking of wood/woodchips. Timber as a log is transported longitudinally through an image detection station with the aid of a CCD camera, by means of which pieces of bark on the surface of the log can be discerned. In this method, a laser bean is used, the trace left by which on the surface of the log is scanned and analyzed. A clean wood surface creates a different kind of image to a bark surface, making analysis possible. If required, the actual bark content can be calculated from the ratio of the surfaces, by using known conversion graphs. A simple surface ratio is sufficient for most purposes. It can be used as a process measurement quantity, while boundary values can be defined for it for adjustment.

Finnish patent application 933517 describes a method for determining the proportions of the differently-colored surfaces of pieces in a flow of material. According to an example, the measurement of the wood content of bark chips takes place by leading the flow of material through two image detection chambers, the first of which has a wood-colored background and the second has a bark-colored background. From the intensity of the reflection, it is possible to determine the relative proportions of both components.

All known on-line methods have the drawback of random disturbances in the image, such as shadows appearing in a flow of chips, or points of discontinuity appearing on the surface of a log.

This invention is intended to create a new kind of method and equipment, by means of which a flow of woodchips, bark material, or logs can be more accurately analyzed than previously, to determine the bark/wood ratio.

SUMMARY OF THE INVENTION

The present invention provides an on-line method and equipment for determining the wood-bark ratio from a flow of material containing timber and bark, such as from a woodchip, bark, or log conveyor, in which method the flow of material is illuminated and scanned using a CCD camera, by which means 30–300 image pixels/cm are obtained in the transverse direction of the flow of material, and the ratio is determined from the ratio of pixels with light and dark images.

Herein this description, the wood-bark ratio means either the bark content of woodchips and logs, or the wood content in bark material. Furthermore, as is known, an ordinary CCD camera has an array of pixels and each pixel detects the gray scale of a certain point, depending on the camera's dynamic range. As is known, an 8 bit camera system detects 256 values of gray scale for each pixel (2 power 8 is 256).

In carrying out the above object and other objects of the invention, an on-line method for determining the wood-bark ratio in a flow of material containing both wood and bark, such as from a woodchip, bark, or log conveyor, includes illuminating the flow of material and scanning the illuminated material using a CCD camera. Thereby, 30–300 image pixels/cm are obtained in the transverse direction of the flow of material, and the bark ratio is calculated from the ratio of pixels depicted as light and dark. In accordance with the method, narrow transverse groups of 1–20 adjacent pixels, in which the brightness or gray scales values of the pixels deviates from a preset criterium are filtered out of the transverse group of pixels and the calculation of the wood-bark ratio of the photographs takes place without these narrow groups.

In one embodiment, a yellow light, with a wavelength range of 620 nm±60 nm, is used to illuminate the material, in which case the contrast between the wood and bark is greatest.

One or more sodium lamps may be used and that the photography is synchronized with their alternating current power supply.

When measuring the bark content of woodchips, the method includes repeating the photography and calculation at least 1000 times to obtain a statistical average of the wood-bark ratio. Preferably, the photography and calculation are repeated in the range of 2000–10,000 times to obtain the statistical average of the wood-bark ratio.

In an alternative method for measuring the bark content of woodchips, the chip pieces are turned onto their sides in relation to the direction of photography, to eliminate the shadows cast by vertical chip pieces. In accordance with this method, the flow of material is directed onto a sloping plate, where the chip pieces fall onto their sides.

In carrying out the method, the color and brightness of the background can be adjusted to be closer to the dominant part of the flow of material. Preferably, several boundaries limits of the light range are set to the brightness of the pixel images to record the images in more than one class, bark wood background so that at least one of the bark, wood, and background can be distinguished from one another.

In what follows, the invention is illustrated with the aid of examples, to which the accompanying Figures refer.

DETAILED DESCRIPTION OF THE INVENTION

Figure 1:
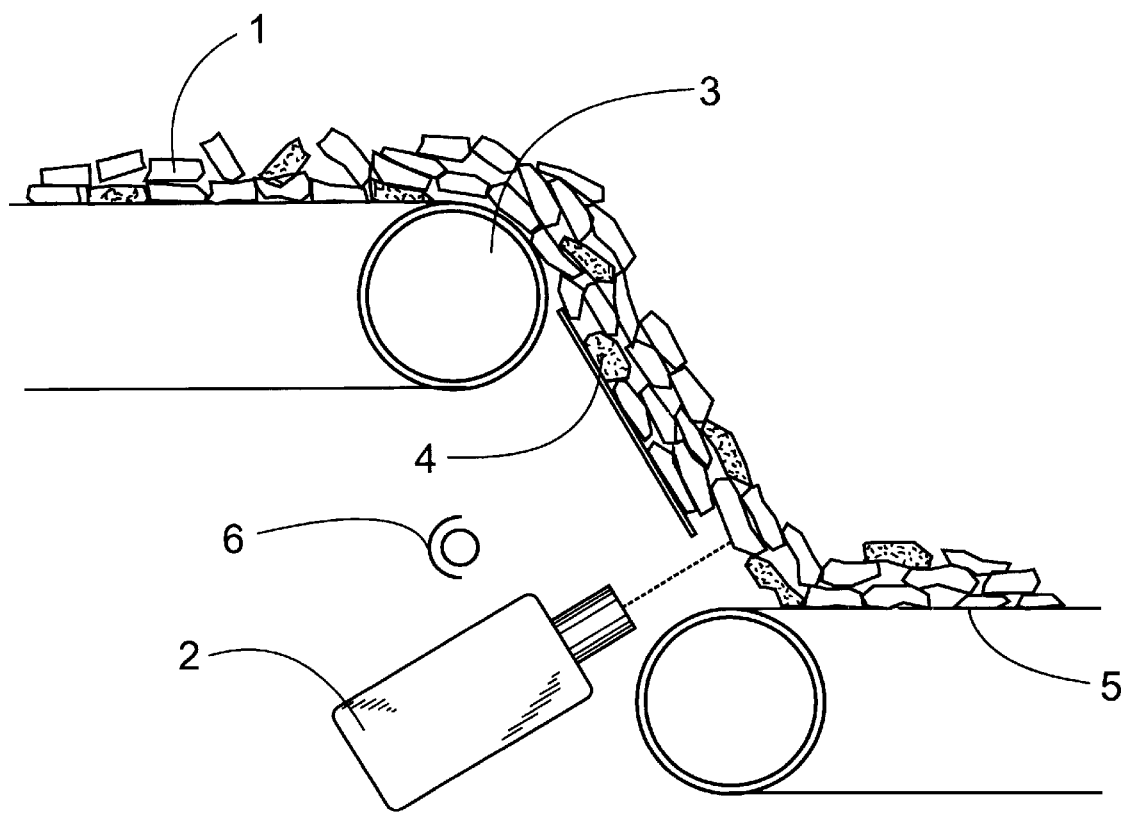
FIG. 1 shows the measurement system in connection with a flow of woodchips.

Referring now to the drawings in detail, in a simple system, a camera is set above a conveyor transporting woodchips or bark material. The method is directly applicable as such to scanning the bark material of a debarking plant, because the difference in size between pieces of wood and bark is so great that special arrangements are generally not needed. However, in woodchips, the surface of the bark may be either large in relation to the chip pieces, or small in relation to the shadows cast by a chip piece. In particular, chip pieces that stick up cast strong shadows, which it should be possible to eliminate.

In the equipment in FIG. 1, the flow of material 1 arrives on the first conveyor, at the end of which there is a pulley wheel 3, on which the chip pieces more easily fall on their sides when the wheel rotates, this being followed by a plate 4, along which the chips slide. At the end of this plate, the chips drop freely for a short distance onto the next conveyor. Between these, it is possible to photograph the under surface of the chips.

Here CCD line cameras can be used, which have a resolution of, e.g. 512, 1024, or 2048 pixels. Each pixel has usually 256 shades of grey. When scanning a 25 cm flow of woodchips, the picture area is $0.1 \times 0.1$ mm$^2$, but with an exposure of 6 ms and a flow of woodchips moving at 2 m/s, the picture area is extended to 12 mm. The normal speed of operation of a CCD camera is 150 pictures per second, permitting the use of conveyor speeds of up to 3 m/s.

The object being scanned is illuminated with a sodium lamp 6, the light from which gives the greatest contrast to wood and bark. At present, it is not really worthwhile using laser light, because red light has a low contrast with both wood and bark. As laser technology develops, laser light too may become applicable, provided the wavelength is suitable. If white light is used, an infrared (IR) filter (less than 400 nm) should be used to filter out the infrared waves. This will improve the contrast in the object. It is generally best to carry out the photography in a wavelength range of 620 nm±60 nm. It is, as such, of no consequence whether the sensitivity of the camera is set to this range, or whether the flow of material is illuminated with light of this range.

Because low-pressure sodium lamps require an alternating current power supply, the flicker caused by this must be synchronized with the camera shutter.

Chip pieces that stick up cast shadows that are so big that it is difficult to filter them out. Due to this, an arrangement according to FIG. 1 is necessary. In it, the chip pieces fall on their sides against the carrier surface. The shadows of chip pieces lying on their side are, on the other hand, quite small and it is possible to filter them out with the aid of a suitable technique. This takes place by, for example, combining 17 pixels into one, in an image taken by a camera containing 2048 pixels, so that only dark areas having an area width of, for example, at least 10 pixels, are included in the calculation. The narrow areas of shadow can then be left out of account and only areas showing a real bark surface are included in the calculation. After the transverse image signal has been corrected of narrow peaks, it is possible to calculate the brightness averages in sequential series of 17 pixels over the entire width of the camera. Generally, narrow groups formed by 1–20 adjacent pixels, in which the brightness of the pixels differ from the background by a preset criterium, are filtered out of the transverse group of pixels, and the calculation of the wood-bark ratio of the image takes place without these narrow groups.

The CCD camera used is itself able to take 15 photographs and calculate the aforementioned average, which it transmits to the computer for calculation. The computer continuously calculates the average on the basis of the results of the last 10,000 photographs. Due to the great dispersion of the subject of the photography, at least 1000 photographs are needed to ensure the reliability of the gray scale measurement. The most advantageous number is 2000–10,000. The image width used in the calculations is the aforementioned 17 pixels, even if the information contained in the image has possibly been filtered in the aforementioned manner. Thus, the area of the image becomes $1.7 \times 12$ mm. This area is generally less than 10% of the projection surface of the woodchips. In any event, the image surface area should be less than 15 %. In practice, the minimum value is determined by the efficiency of the calculation. Using a modern PC-based system, the relevant value is 1–10%, when an appropriate result is obtained.

The color of the background should be adapted according to the dominant part. This means, that when a flow of wood chips is being scanned, a light background should be used, but when scanning bark material, a dark background is used. In more highly-developed systems, the share of the background as different degrees of darkness can be recorded in its own class, as can, perhaps, shadows.

It is possible to apply the technique used more or less as such to the photography of a flow of logs, if the logs are transported in a longitudinal direction. The width of the logs then corresponds, in size class, to the widths used of the flow of woodchips or bark. Pieces of bark visible in the images are often only slightly larger than the bark pieces visible in woodchip pieces. The photography can be carried out by using either a single camera and simultaneously rotating the logs, or three cameras, according to FIG. 2.

Figure 2:
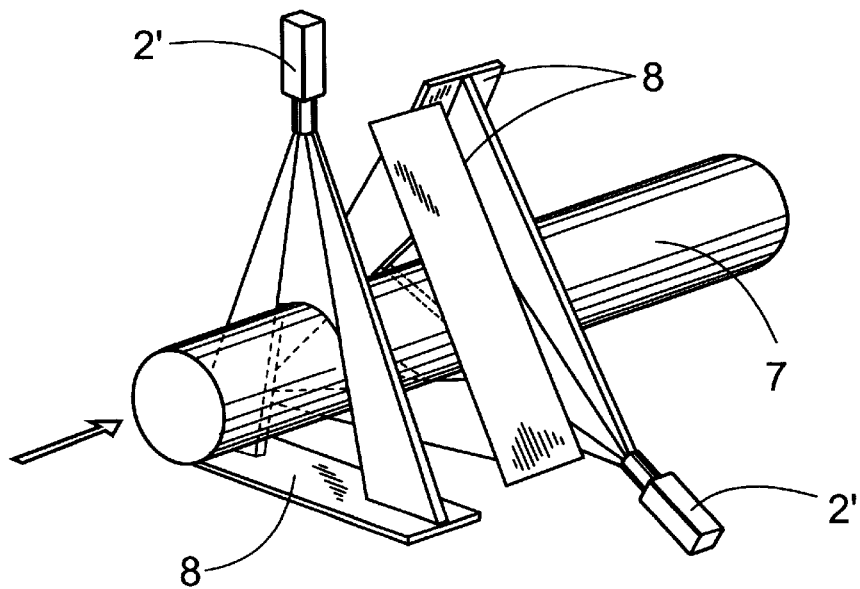
FIG. 2 shows a three-camera system adapted to scanning a log.

In FIG. 2, the log is marked with the reference number 2 and it is moved longitudinally through the scanning area. The cameras 2' are arranged at an angle of 120° to one another on different sides of the log, while on the opposite side of the log there is a scanning background 8. Only wooden material can be reliably seen against a black background. Because of this, log diameter data is used in the calculations, which is obtained in a conventional manner in another way.

The method and equipment according to the invention also permit so-called precision debarking and evaluation of the quality of the logs. Points in a log seen, during scanning, to have bark can be recorded and efficient further debarking can be directed to only these points. On the other hand, the photographs reveal knots, which provides information on the quality of the log.

Although the invention has been described by reference to a specific embodiment, it should be understood that numerous changes may be made within the spirit and scope of the inventive concepts described. Accordingly, it is intended that the invention not be limited to the described embodiment, but that it have the full scope defined by the language of the following claims.

What is claimed:

1. An on-line method for determining the wood-bark ratio in a flow of material containing both wood and bark, such as from a woodchip, bark, or log conveyor, comprising the steps of:

illuminating the flow of material;

scanning the flow of material with a linear array CCD camera;

obtaining 30–300 image pixels/cm in the transverse direction of the flow of material;

measuring the shade of grey of each pixel;

grouping the pixels according to gray scale values measured into groups;

identifying narrow sub-groups within each group whose grey scale value deviates from a background preset criterium, a maximum number of pixels of a sub-group being 20 adjacent pixels;

filtering out the identified sub-groups from the groups;

calculating a brightness average of the pixels remaining in each group over an entire width of the camera based on the gray scale values of those remaining pixels; and subsequently calculating a wood-bark ratio from the calculated brightness averages of the groups without these narrow sub-groups;

wherein the bark ratio is determined from the ratio of pixels detected as light and dark.

2. The method of claim 1 wherein illuminating the flow of material includes illuminating with a yellow light source having a wavelength range of 620 nm±60 nm.

3. The method of claim 2 wherein the yellow light source is at least one sodium lamp and the imaging is synchronized with their alternating current power supply.

4. The method of claim 1 wherein the imaging and calculating are repeated at least 1000 times to obtain a statistical average of the wood-bark ratio.

5. The method of claim 1 wherein the imaging and calculating are repeated in the range of 2000–10,000 times to obtain a statistical average of the wood-bark ratio.

6. The method of claim 1 wherein the material in the flow is turned onto its side in relation to the direction of photography, to eliminate shadows cast by vertical chip pieces.

7. The method of claim 6 wherein the flow of material is directed onto a sloping plate, causing the chip pieces to fall onto their sides.

8. The method of claim 1 comprising the step of adjusting the color and brightness of the background to be closer to the dominant part of the flow of material.

9. The method of claim 1 comprising the step of defining brightness classes for wood and bark for identifying pixel groupings.

10. The method of claim 9 comprising the step of setting boundaries relative to the pixel grey scale values and distinguishing background from material flow.

\* \* \* \* \*